US008475167B2

(12) United States Patent
Dunn

(10) Patent No.: US 8,475,167 B2
(45) Date of Patent: Jul. 2, 2013

(54) MAGNETICALLY IMPLANTABLE PROSTHETIC DEVICE AND METHOD TO SHORTEN HEALING TIME, ENHANCE BONE FUSION, AND RETARD BACTERIAL GROWTH

(75) Inventor: Frederic B. Dunn, Gulfport, MS (US)

(73) Assignee: Frederic B. Dunn, Memphis, TN (US)

( * ) Notice: Subject to any disclaimer, the term of this patent is extended or adjusted under 35 U.S.C. 154(b) by 667 days.

(21) Appl. No.: 12/216,261

(22) Filed: Jul. 2, 2008

(65) Prior Publication Data
US 2009/0029316 A1   Jan. 29, 2009

Related U.S. Application Data

(60) Provisional application No. 60/929,563, filed on Jul. 3, 2007.

(51) Int. Cl.
*A61C 8/00* (2006.01)
(52) U.S. Cl.
USPC .......................................................... 433/173
(58) Field of Classification Search
USPC ................ 433/172–176, 199.1, 200.1, 201.1, 433/215
See application file for complete search history.

(56) References Cited

U.S. PATENT DOCUMENTS

| 4,195,367 | A | * | 4/1980 | Kraus | 623/23.49 |
| 4,214,322 | A | * | 7/1980 | Kraus | 623/23.49 |
| 4,214,366 | A | * | 7/1980 | Laban | 433/189 |
| 4,216,548 | A | * | 8/1980 | Kraus | 623/23.49 |
| 4,508,507 | A | * | 4/1985 | Jackson | 433/189 |
| 4,626,213 | A | * | 12/1986 | Shiner et al. | 433/173 |
| 4,693,686 | A | * | 9/1987 | Sendax | 433/173 |
| 4,702,697 | A | * | 10/1987 | Linkow | 433/173 |
| 4,993,950 | A | * | 2/1991 | Mensor, Jr. | 433/173 |
| 5,292,252 | A | * | 3/1994 | Nickerson et al. | 433/173 |
| 5,421,722 | A | * | 6/1995 | Stemmann | 433/189 |
| 5,725,377 | A | * | 3/1998 | Lemler et al. | 433/173 |
| 5,871,357 | A | * | 2/1999 | Tseng | 433/189 |
| 5,954,506 | A | * | 9/1999 | Tanaka | 433/214 |
| 6,032,677 | A | * | 3/2000 | Blechman et al. | 128/899 |
| 6,034,295 | A | * | 3/2000 | Rehberg et al. | 623/23.49 |
| 6,540,515 | B1 | * | 4/2003 | Tanaka | 433/189 |
| 7,917,223 | B2 | * | 3/2011 | Madjar et al. | 607/51 |
| 2002/0137010 | A1 | * | 9/2002 | Honkura et al. | 433/189 |
| 2004/0063072 | A1 | * | 4/2004 | Honkura et al. | 433/189 |

* cited by examiner

*Primary Examiner* — Cris L Rodriguez
*Assistant Examiner* — Hao D Mai
(74) *Attorney, Agent, or Firm* — Carmen Patti Law Group, LLC

(57) ABSTRACT

A prosthetic implant is provided that has an implantable magnetic base structure that supports or couples with a prosthetic superstructure for implantation in a mammal. The implantable base more quickly fuses with surrounding tissue or bone with the aid of a magnetic field. The superstructure abuts and is supported by the implantable base, and each comprises a biocompatible magnetic material to establish a magnetic field in the region of the tissue surrounding the implantable base. An anchoring arrangement may be employed to fasten the superstructure to the base. Together, the magnetic base, superstructure, and/or anchoring arrangement are positioned relative to each other to concentrate a magnetic field in the region of the implant to facilitate fusion of the base structure with surrounding bone or tissue. Advantageously, the magnetic field shortens the healing time and retards bacterial growth to quickly fuse the base structure with the surrounding bone or tissue.

12 Claims, 6 Drawing Sheets

MAGNETICALLY IMPLANTABLE PROSTHETIC DEVICE AND METHOD TO SHORTEN HEALING TIME, ENHANCE BONE FUSION, AND RETARD BACTERIAL GROWTH

CROSS-REFERENCE TO RELATED APPLICATION

This invention claims the benefit of U.S. Provisional Application Ser. No. 60/929,563 filed Jul. 3, 2007 in the name of the same inventor hereof.

BACKGROUND OF THE INVENTION

The present invention relates to a prosthetic device and a method of healing, but more specifically to an implant that produces a magnetic field in a region of surrounding tissue or bone to aid the healing process. The magnetic field interacts with calcium ions in the region of the implant in order to shorten overall healing time, retard bacterial growth, and speed up fusion of bone or tissue to an implantable base structure.

This invention is illustrated in a dental application but has application to mammalian implants generally.

As known in the art, surgical placement of medically necessary oral implants requires an osteotomy (hole) in the bone of the maxillary or mandibular alveolus jaws. Once the size of the surgical site has been achieved and accessed, a recovery or healing phase follows to allow the implants to osseous integrate or fuse the bone with a biocompatible implanted material. This process requires a certain amount of healing time, the duration of which depends on the patient's ability to heal and counter bacterial growth.

A totally magnetic implant system according to the present invention reduces healing time and can be made of, but not limited to, sintered hard ferrite/ceramic, sintered, rare earth bonded alnico, or flexible magnets and their assemblies. The inventive implant may comprise either isotropic or anisotropic properties. The ensuing magnetic and electromagnetic field will aid in the art of healing. Electric or magnetic stimulus of the tissue causes bone to heal or osseointegrate at a faster rate.

According to the present invention, techniques that promote osseointegration include increasing the surface area of the implant using, for example, acid etching or plasma spraying. A coating material such as HA (hydrorylapptite) may also be applied to the implant to assist osseointegration. Electrical or magnetic stimulus from the magnetic implant induce fibroblast to lay down fibrin (glue) which forms a bridge or scaffold between bone and the implant. The stimulus causes bone fusion of the implant (stability) in a shorter time.

If bacteria grow in the implanted region, it may either delay healing or cause total failure of the healing process. The electromagnetic or magnetic field produced by the inventive implant, on the other hand, effectively produces a bacterialcidal or bacterial static environment that retards or stops interference with the healing process.

Once the process of osseointegration is complete, a prosthetic abutment may be secured to the bone-fused implant using screws or other conventional means of anchorage. In the prior art, problems often occur when screws attached directly to bone fracture or become dislodged or unscrewed which, in turn, causes dislodging of the prosthetic abutment from the implant. Utilizing a total magnetic system according to the present invention, however, stabilizes the implant and prosthetic abutment.

European practitioners have been using medical magnetic fields for years (see Dr. William Pawluk's article, www.naturalhealthweb.com/articles/pawluk1.html). Magnetic fields provide beneficial results by electrically stimulating a mammal's immune system in the affected region.

It was not know in the past, however, to use magnetic elements for substructural and superstructural components of an implant system or to arrange magnetic components to focus a magnetic field at an interface region between an implantable base and surrounding tissue to facilitate healing or to fight bacterial infection in the implant region. Prior use of magnetic fields within the context of prosthetics was primarily limited to affixation. Some are disclosed in U.S. Pat. Nos. 4,258,705 to Sorensen et al., 5,507,835 to Jore, 4,693,686 to Sendax, 4,214,366 to Laban, 4,302,189 to Gillings, 5,611,689 and 5,425,763 to Stemmann, 6,187,041 and 2001/0046205 to Garnozik, and 6,275,736 to Kuzma. These devices employed magnets to stabilize the position of at least a portion of a prosthetic device, either by using attractive magnetic forces to bind together more securely a base implant and prosthesis or by using repulsive magnetic forces to relieve pressure the implant may impose on surrounding tissue during healing. In addition, prior techniques to aid osseointegration of surrounding tissue with the implant involved acid etching or plasma spraying to increase the surface area of the implant to which bone may fuse.

The present invention, on the other hand, provides a method or system to utilize magnetic implants to both anchor and heal; and also to establish a concentrated magnetic field in the tissue region to facilitate fusion of tissue with the implantable base. The magnetic field also establishes a retardant to bacteria that might otherwise interfere with healing and fusion.

These goals are achieved using a biocompatible material for the base substructure as well as for a prosthetic superstructure that may abut the substructure. Each component is positioned relative to the other to establish predictable magnetic fields in the tissue region.

SUMMARY OF THE INVENTION

According to the present invention, there is provided a method of reducing healing time and facilitating bone fusion to an implantable device comprising the steps of providing a magnetic base structure of an implant of a biocompatible magnetic material, providing a magnetic superstructure of said implant that mates with the base structure, and implanting the superstructure and base structure in a mammal whereby to reduce healing time by enhancing bone fusion of the mammal to the implantable part and to generate a bacteriostatic environment that reduces bacterial interference with the healing process.

Another aspect of the present invention comprises a prosthetic assembly to provide a stable environment for healing. The assembly comprises an implantable base structure of a biocompatible magnetic material, a magnetic superstructure that mates with the base; and an internal design to anchor the base structure to the superstructure, and internal design whereby the base structure, superstructure, and anchor are arranged in a way to establish a magnetic field in tissue region of the mammal to reduce healing time and to provide a bacterial static environment that prevents bacterial growth from inhibiting the healing process. The implantable base may be in the form of a screw that aids anchoring while healing. If multiple implants are placed during healing the base may be splinted together to provide additional stability.

Other aspects of the invention will become apparent upon review of the following description taken in connection with the accompanying drawings. The invention, though, is pointed out with particularity by the appended claims.

DESCRIPTION OF ILLUSTRATIVE EMBODIMENTS

Figure 1:
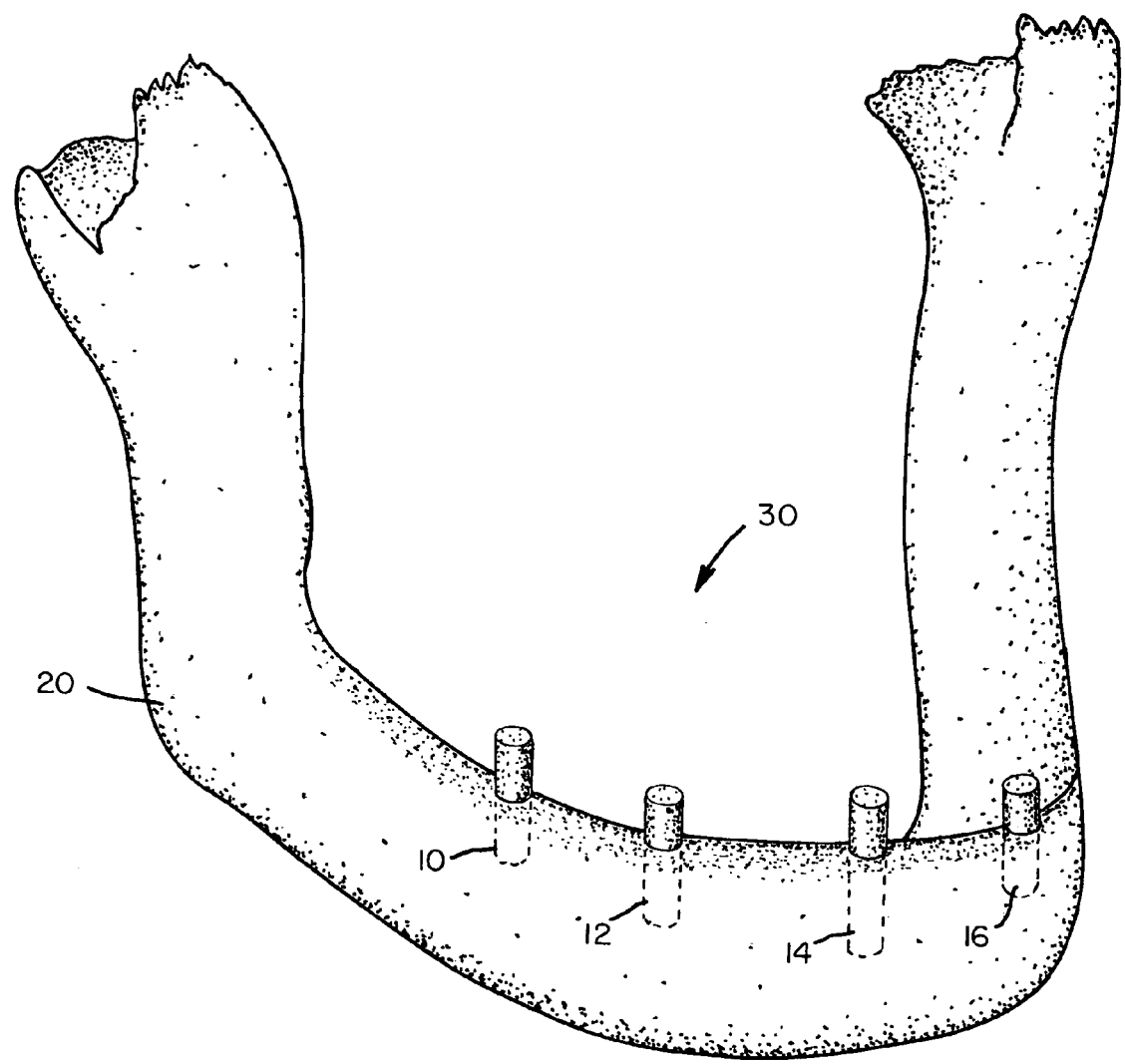
FIG. 1 illustrates a mandibular implant including magnetic posts according to one embodiment of the present invention.
Figure 2:
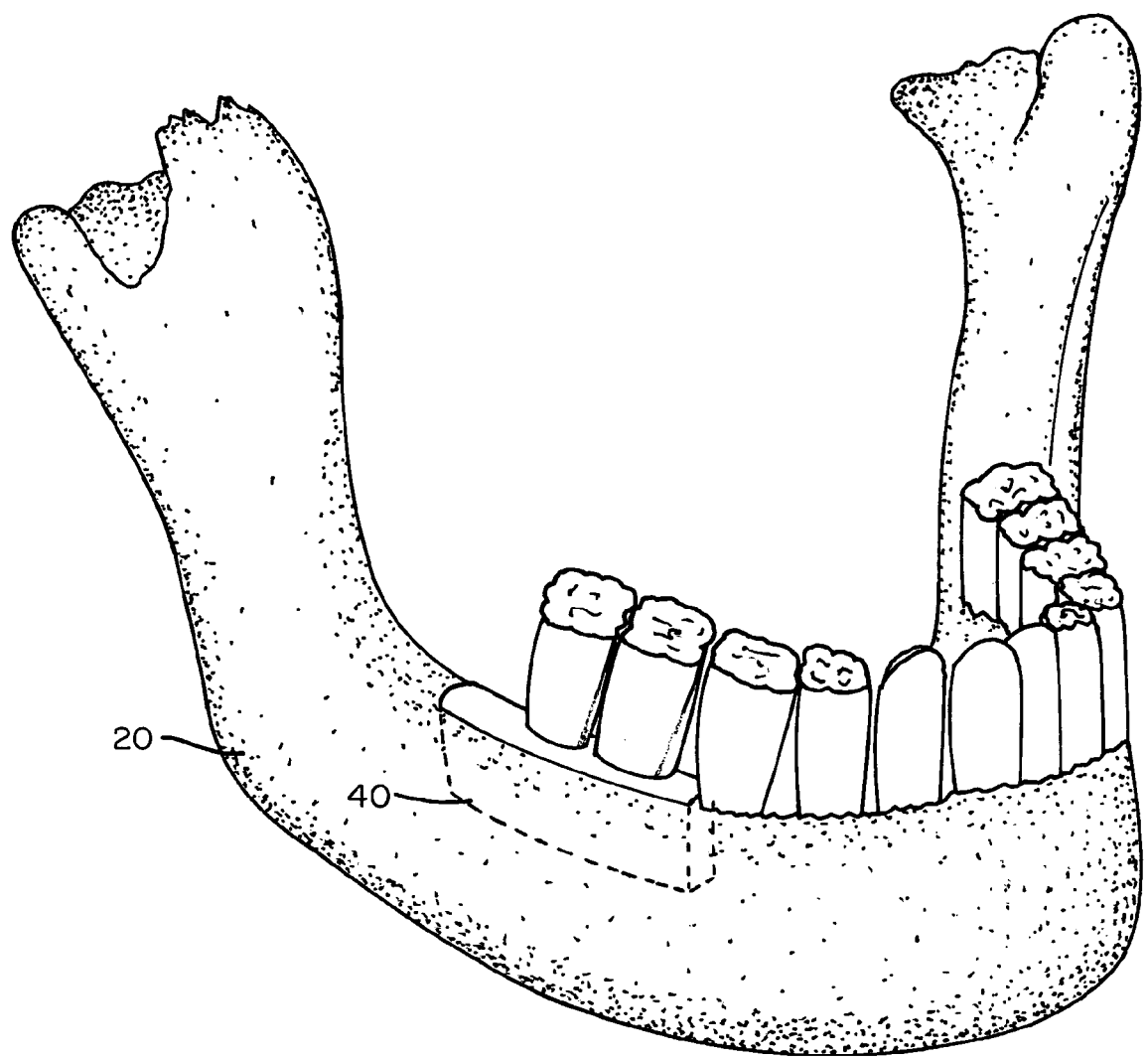
FIG. 2 illustrates a mandibular implant including magnetic posts according to another embodiment of the present invention.

A first illustrated embodiment of the invention facilitates healing in the oral cavity of mammal, but is not limited to that region. FIG. 1, for example, shows a subperiosteal implant comprising a number of magnetic posts 10; 12, 14 and 16 as part of a biocompatible framework (e.g., magnetic) implanted into a mandibular 20 to support dentures generally indicated at 30. FIG. 2 shows an endosteal implant comprising a magnetic plate 40 implanted directly into mandibular 20 to provide a base structure upon which to affix dentures or teeth. The implant may also be placed in the maxilla. Surgical procedures to implant the framework or plates entails cutting or drilling the site to receive the implant, after which there is a period of healing phase during which osseointegration occurs to fuse the implanted base structure to bone. Preferably, a biocompatible material is used for the magnetic components of the implant. These materials may be isotropic or anisotropic, but not limited to these properties.

Providing a magnetic material of an implant for an endosteal, blade, subperiosteal, transosted or any other type of surgical implant improves healing in the oral cavity. Electrical or magnetic stimulus will first attract red blood cells (due to iron in hemoglobin) which are the bases of blood clotting and induce fibroblast to lay down fibrin (a glue-like substance) that starts the fusion process and also to stimulate the healing process. Bacteria are known to interfere with the healing process by causing delay or failure of fusion. Electrical or magnetic fields, however, produce a bacterialcidal or bacteriostatic environment that stops or retards such interference. Once osseointegration is complete, the prosthetic superstructure may be secured to the implanted substructure by magnetic attraction and an internal anchor design. Further, to assist in osseousintegration of bone to the implanted substructure, the surface of the implant may be treated with hydroxyl appitite, ascorbic acid, or platelet rich plasma prior to implant to increase the effective surface area to which bone will fuse.

Electrical and magnetic stimuli helps the healing process by promoting osseointegration at a faster rate. The process is believed to provide an increase in ionic activity in the surgical region which is responsible for stimulating healing.

Figure 3A:
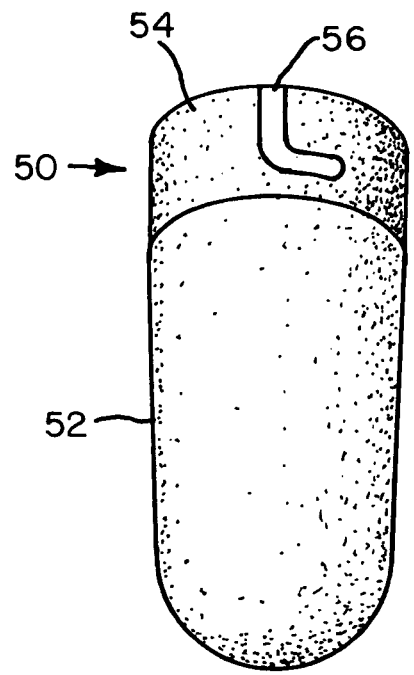
FIGS. 3A and 3B illustrate an embodiment of an implant in accordance with the principles herein.
Figure 3B:
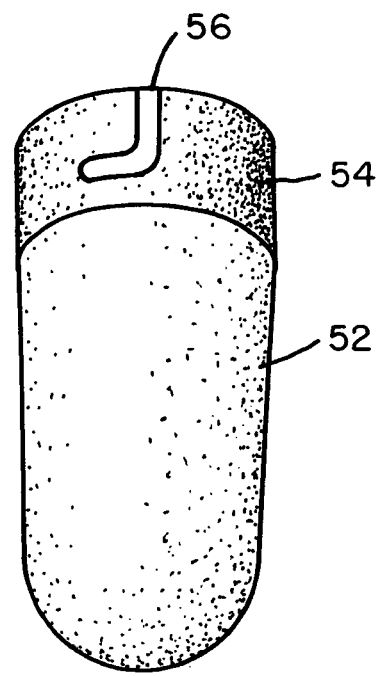
Figure 3C:
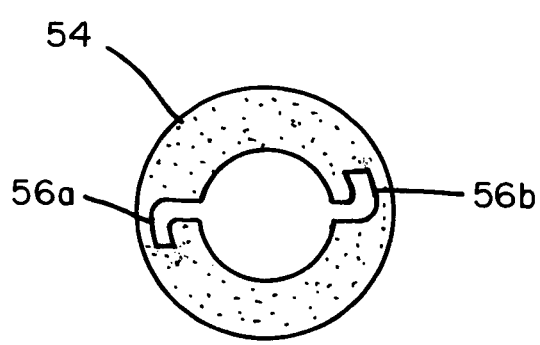
FIG. 3C illustrates a top view of the implant of FIGS. 3A and 3B.
Figure 3D:
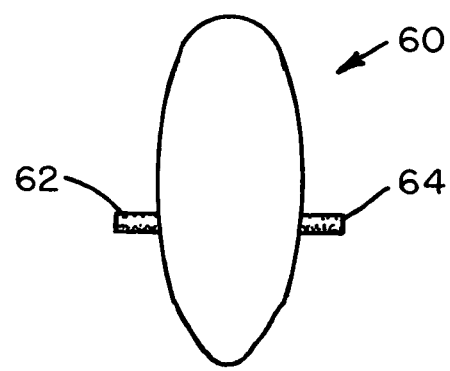
FIG. 3D illustrates a prosthesis which can be used with the implant of FIGS. 3A and 3B.

FIGS. 3A, 3B and 3C show an exemplary base or substructure having an implanted region 52 and having an integrated cap 54. When implanted, the region 52 is surrounded by tissue or bone. FIG. 3D, on the other hand, shows a superstructure 60 in the form of a denture or tooth that may be affixed to the implantable base structure 50. Implantable base 52 and superstructure 60 each comprise a biocompatible magnetic material, as explained above. Region 52 of implantable base 50 may be treated or coated as explained above to increase its effective surface area, which enhances fusion of region 52 with surrounding tissue or bone. Cap 54 of the implantable base, as best shown in FIG. 3C, includes an exemplary anchoring arrangement comprising opposing slots 56a and 56b (e.g. receptors) that receive anchor posts 62 and 64 (e.g. donors) of a superstructure 60 (FIG. 3D) in order to affix superstructure 60 to implantable base 50. Components of the anchoring arrangement may also comprise biocompatible magnetic materials, as well as posts 62 and 64, to facilitate affixation and/or to help focus the magnetic field in the region of the base structure.

Biocompatible materials may be selected from a group of materials comprising hard ferrite ceramic material, sintered rare earth materials, alnico, flexible magnets and their assemblies, and other materials providing the same or similar properties. The base structure, superstructure, and any associated anchorage system (e.g., pins, fins, clamps, screws, etc.) preferable are all magnetic (but portions thereof need not be), thereby helping to direct or focus a powerful magnetic field around the tissue region of the implant. As indicated above, the magnetic field shortens healing time of the affected area and creates a bacteriostatic environment to further ensure success of the implant and prosthetic superstructure.

In another aspect of the invention, a method of facilitating healing includes forming an implantable base, abutment, and anchorage arrangement from a material selected from the group comprising but not limited to hard ferrite ceramic, sintered rare earth, alnico, flexible magnets and their assemblies; implanting the base into a mammal; affixing a superstructure to the base using an anchoring arrangement, and positioning the base, abutment, and anchoring arrangements in a way to direct or focus a magnetic field in the region of the tissue of bone surrounding the base. Alternatively, the method comprises a step of forming a significant portion (if not all) of the components of the implant from biocompatible materials; magnetizing those parts (if not inherently magnetic) to ensure that the magnetic field of substructure is established to apply an attractive force on a superstructure and/or its anchorage system; and attaching the substructure, superstructure, and anchor to the mammal's body in a way to focus the magnetic field in the region of the implant body. The magnetic field attracts red blood cells; thereby promoting faster healing, preventing bacteria from attacking that region, and encouraging quicker bone fusion to the implant.

While one embodiment of invention is illustrated in connection with the maxillary and mandibular areas of the body, magnetic healing disclosed herein are applicable to any region of the body. It is important that the magnetic poles of the base substructure and the prosthetic abutment are opposing to ensure interlocking and to create an intense flux density in the region of the implant. Magnetic fields attract or repel ions subjected to the field, which are active in numerous cellular chemical processes such as healing. The substructural base implant, prosthetic superstructure device, and anchorage system are arranged to create a bipolar magnetic environment thereby creating a predictable ionic transfer within the region of the magnetic field.

Figure 4:
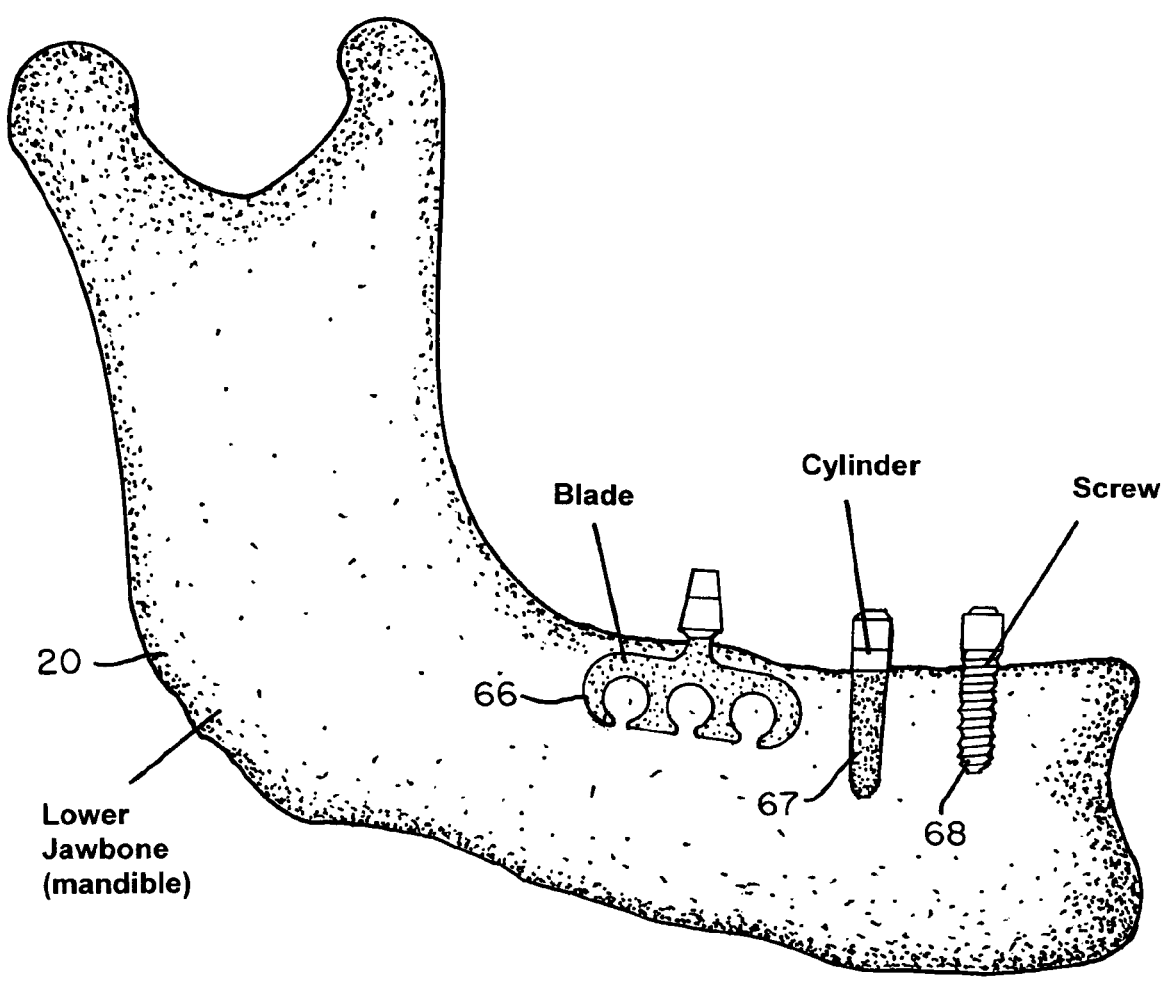
FIG. 4 illustrates various types of conventional endosseous implants that may be positioned in jawbone to form a substructure to which a prosthesis may be affixed.
Figure 5:
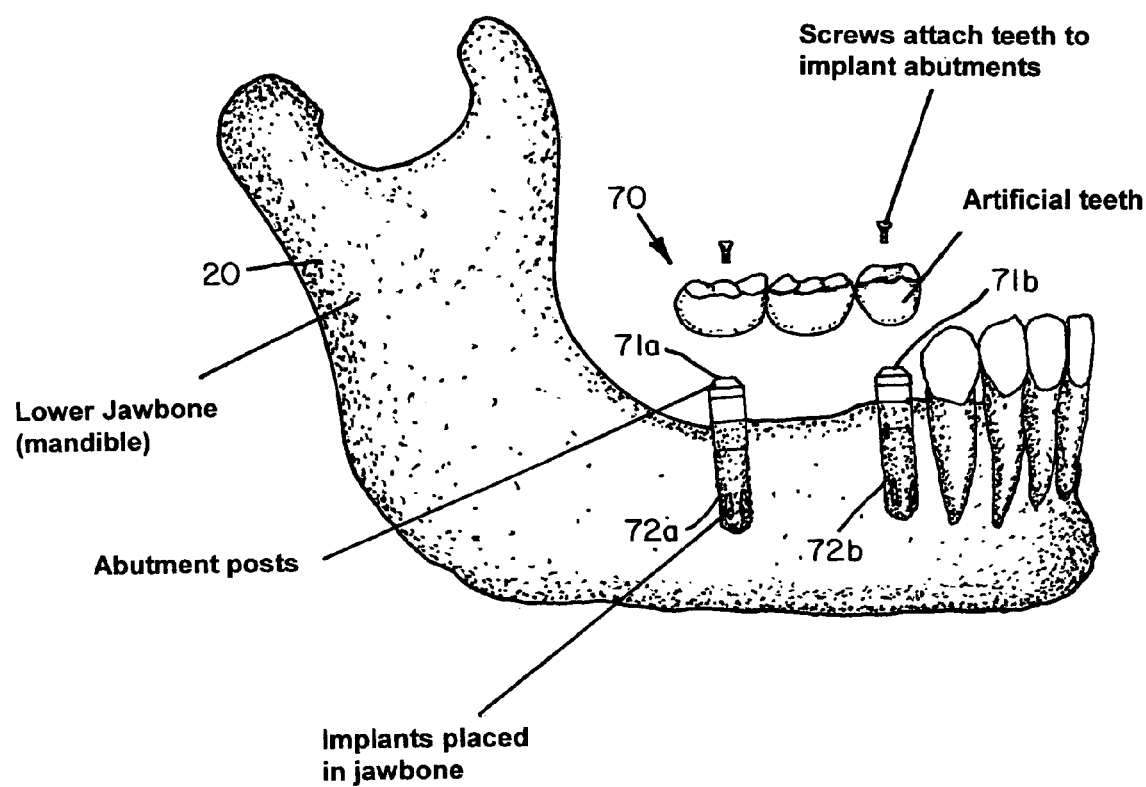
FIG. 5 illustrates a prosthetic abutment comprising a group of three artificial teeth that may be affixed to posts of a pair of cylinder implants of in a jawbone.
Figure 6:
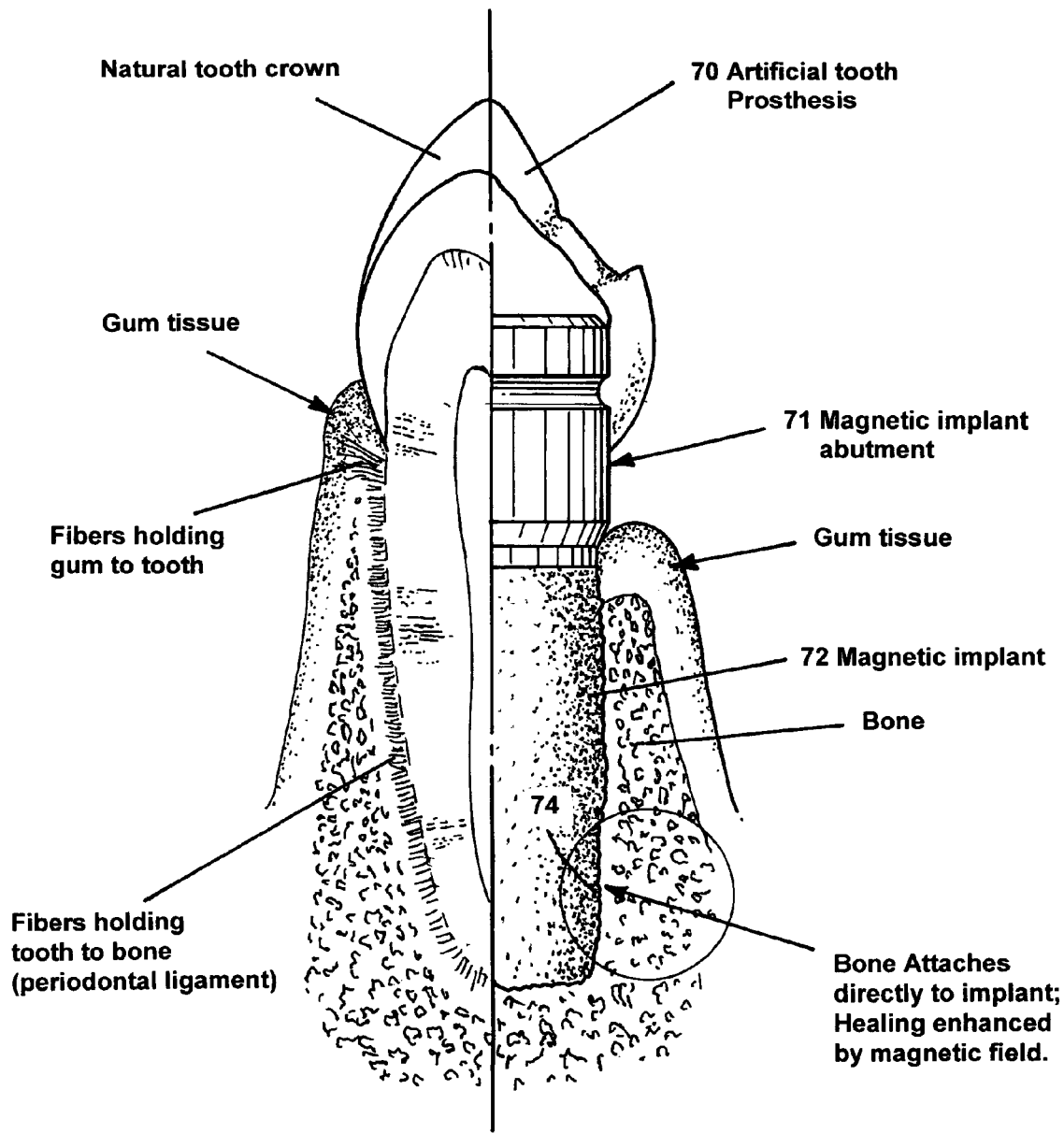
FIG. 6 illustrates a region of osseointegration and healing to which a magnetic field may be applied by magnetic components of an implant and/or abutment.

FIG. 4 shows various types of conventional endosseous implants that may be positioned in jawbone 20 to form a substructure to which a prosthesis may be affixed. Illustrated implants include a blade 66, cylinder 67, and screw 68. According to the present invention, however, each of the implants 66-68 may comprise a magnetic material to form a magnetic field about a region of healing. FIG. 5 show a prosthetic superstructure comprising a group 70 of three artificial teeth that may be affixed to abutments 71a and 71b of a pair of cylinder implants 72a and 72b of jawbone 20. According to the present invention, either or both the posts 72 (collectively) and/or the abutments 71 (collectively) may be magnetic to also produce a magnetic field about a region of healing. FIG. 6, where like reference numerals represent like elements, is provided to illustrate a region 74 of osseointegration and healing to which a magnetic field may be applied by magnetic component of the implant 72 and/or abutment 71.

While the illustrated invention discloses a specific application or use, it will be understood that, based on the teachings herein, variations thereof by those skilled in the art are embraced within the scope of the appended claims.

What is claimed is:

1. A method of implanting a dental implant in the maxillary or mandibular jaws of a mammal so as to promote-reduced healing time and improved bone fusion comprising the steps of:
    providing a magnetic base structure having a body that is formed substantially of a biocompatible magnetic material, said magnetic base structure comprising a portion of the implant that is configured to be inserted into a cavity in the jawbone into which it is implanted;
    providing a receptor device adapted to be attached to said magnetic base structure;
    providing a prosthesis, said prosthesis including a donor device configured to be removably attached to said magnetic base structure, said prosthesis further including one or more replacement teeth;
    implanting the magnetic base structure in said cavity in the jawbone of the mammal to promote osseointegration, reduce healing time and enhance bone fusion with surrounding tissue or bone by establishing a bacteriostatic environment that reduces bacterial interference with a healing process; and
    attaching said prosthesis to said magnetic base structure utilizing said donor device and receptor device.

2. The method as recited in claim 1, wherein said magnetic base structure comprises a material selected from the group comprising ferrite ceramic, sintered rare earth, alnico, and a flexible magnetic material.

3. The method as recited in claim 2, further comprising the step of increasing the effective surface area of said magnetic base structure to improve fusion of said magnetic base structure with surrounding bone or tissue.

4. The method of claim 1 wherein said receptor device further comprises L-shaped slots adapted to receive pins and said donor device further comprises pins.

5. The method of claim 4, further comprising the step of inserting said donor pins into said receptor L-shaped slots to attach the donor device to the receptor device.

6. A dental implant that provides a stable environment for healing when implanted in the maxillary or mandibular jaws of a mammal, said dental implant comprising:
    a magnetic base structure having a body that is formed substantially of a biocompatible magnetic material, said magnetic base structure comprising a portion of the dental implant that is configured to be inserted into a cavity in the jawbone into which it is implanted, said magnetic base structure being arranged in a way to establish a magnetic field in a region of the dental implant to promote osseointegration and reduce healing and fusing time by providing a bacteriostatic environment that prevents bacterial growth from inhibiting the healing process;
    an abutment attached to said magnetic base structure, said abutment forming a receptor device; and
    a superstructure including a donor device for cooperatively interacting with the receptor device, said superstructure further including one or more prosthetic teeth attached to said donor device.

7. The dental implant as recited in claim 6 wherein said magnetic base structure includes a treated surface to increase effective surface area thereof and to improve fusion with surrounding tissue or bone.

8. The dental implant of claim 6, wherein said implantable base structure comprises a material selected from the group comprising ferrite ceramic, sintered rare earth, alnico, and a flexible magnetic material.

9. The dental implant as recited in claim 6 wherein said magnetic base structure is treated prior to implant with any one of hydroxyl appitite, ascorbic acid or platelet rich plasma.

10. The dental implant as recited in claim 6 wherein said biocompatible magnetic material is not inherently magnetic.

11. The dental implant of claim 6 wherein said receptor device further comprises L-shaped slots adapted to receive pins and said donor device further comprises pins adapted to be inserted into said L-shaped slots.

12. A method of implanting a dental implant having reduced healing time and improved bone fusion comprising the steps of:
    preparing an osteotomy in the jawbone of a mammal to receive the dental implant;
    inserting a magnetic base structure having a body that is formed substantially of a biocompatible magnetic material into said osteotomy, said magnetic base structure coming into direct contact with the jawbone and generating a magnetic field in the location of the jawbone so as to reduce healing time and enhance bone fusion by establishing a bacteriostatic environment,
    leaving said magnetic base structure in said osteotomy for a period of time sufficient to allow healing and osseointegration to take place;
    attaching an abutment to said magnetic base structure, said abutment comprising a receptor device;
    attaching a prosthesis to said abutment, said prosthesis comprising a donor device to attach to the receptor device of the abutment, said prosthesis further comprising replacement teeth attached to said donor device.

* * * * *